United States Patent
Rader et al.

(10) Patent No.: US 6,386,015 B1
(45) Date of Patent: May 14, 2002

(54) APPARATUS TO COLLECT, CLASSIFY, CONCENTRATE, AND CHARACTERIZE GAS-BORNE PARTICLES

(75) Inventors: Daniel J. Rader; John R. Torczynski, both of Albuquerque, NM (US); Karl Wally, Lafayette, CA (US); John E. Brockmann, Albuquerque, NM (US)

(73) Assignee: Sandia Corporation, Livermore (CA)

(*) Notice: Subject to any disclaimer, the term of this patent is extended or adjusted under 35 U.S.C. 154(b) by 0 days.

(21) Appl. No.: 09/469,718

(22) Filed: Dec. 21, 1999

Related U.S. Application Data

(60) Provisional application No. 60/151,815, filed on Aug. 30, 1999.

(51) Int. Cl.$^7$ ................................................ G01N 1/00
(52) U.S. Cl. ................ 73/31.05; 73/23.33; 73/28.01; 73/28.04; 73/28.05; 73/31.02; 73/31.07
(58) Field of Search ........................... 73/23.33, 28.01, 73/28.04, 28.05, 28.06, 31.02, 31.03, 31.05, 31.07, 53.01, 53.07, 61.71, 61.72, 863.21, 863.22

(56) References Cited

U.S. PATENT DOCUMENTS 6,156,212 A * 12/2000 Rader et al. ................ 73/28.05
6,170,342 B1 * 1/2001 John ........................ 73/863.21

OTHER PUBLICATIONS

Torczynski, J.R.; O'Hern, T.J.; Rader, D.J., Brocckmann, J.E.; Glasser, T.W., "An Experimental Investigation of the Flow in a Virtual Cyclone". Sandia Report No. SAND98–2004, 44 pages, printed Sep. 1998.

* cited by examiner

Primary Examiner—Daniel S. Larkin
(74) Attorney, Agent, or Firm—L. E. Carnahan; T. P. Evans

(57) ABSTRACT

An aerosol lab-on-a-chip (ALOC) integrates one or more of a variety of aerosol collection, classification, concentration (enrichment), and characterization processes onto a single substrate or layered stack of such substrates. By taking advantage of modern micro-machining capabilities, an entire suite of discrete laboratory aerosol handling and characterization techniques can be combined in a single portable device that can provide a wealth of data on the aerosol being sampled. The ALOC offers parallel characterization techniques and close proximity of the various characterization modules helps ensure that the same aerosol is available to all devices (dramatically reducing sampling and transport errors). Micro-machine fabrication of the ALOC significantly reduces unit costs relative to existing technology, and enables the fabrication of small, portable ALOC devices, as well as the potential for rugged design to allow operation in harsh environments. Miniaturization also offers the potential of working with smaller particle sizes and lower pressure drops (leading to reduction of power consumption).

61 Claims, 4 Drawing Sheets

FIG. 1

```
                            ┌──────────────┐
                            │  17          │
                            │  TELEMETRY   │
                            └──────▲───────┘
                                   │ 21
                            ┌──────┴───────┐
                            │  SIGNAL  16  │
                            │  PROCESSOR   │
                            └──────▲───────┘
                                   │ 21
  ┌─────────┐   ┌──────────────┐   ┌──────────────┐   ┌──────┐
  │   18    │──▶│  AEROSOL  12 │──▶│ AEROSOL   13 │──▶│ PUMP │──▶
  │ AEROSOL │   │PRECONDITIONER│   │CHARACTERIZATION│ │  14  │
  │  CLOUD  │   └──────▲───────┘   └──────▲───────┘   └──▲───┘
  └─────────┘          │                  │              │
       │ 11            │                  │              │
       INLET           │                  │              │
                       │                  │              │
                       └──────────┬───────┴──────────────┘
                                  │ 21
                          ┌───────┴──────┐
                          │ PROCESS  15  │
                          │ CONTROL      │
                          └───────▲──────┘
                                  │ 20
                          ┌───────┴──────┐
                          │  BATTERY  19 │
                          └──────────────┘
```

10

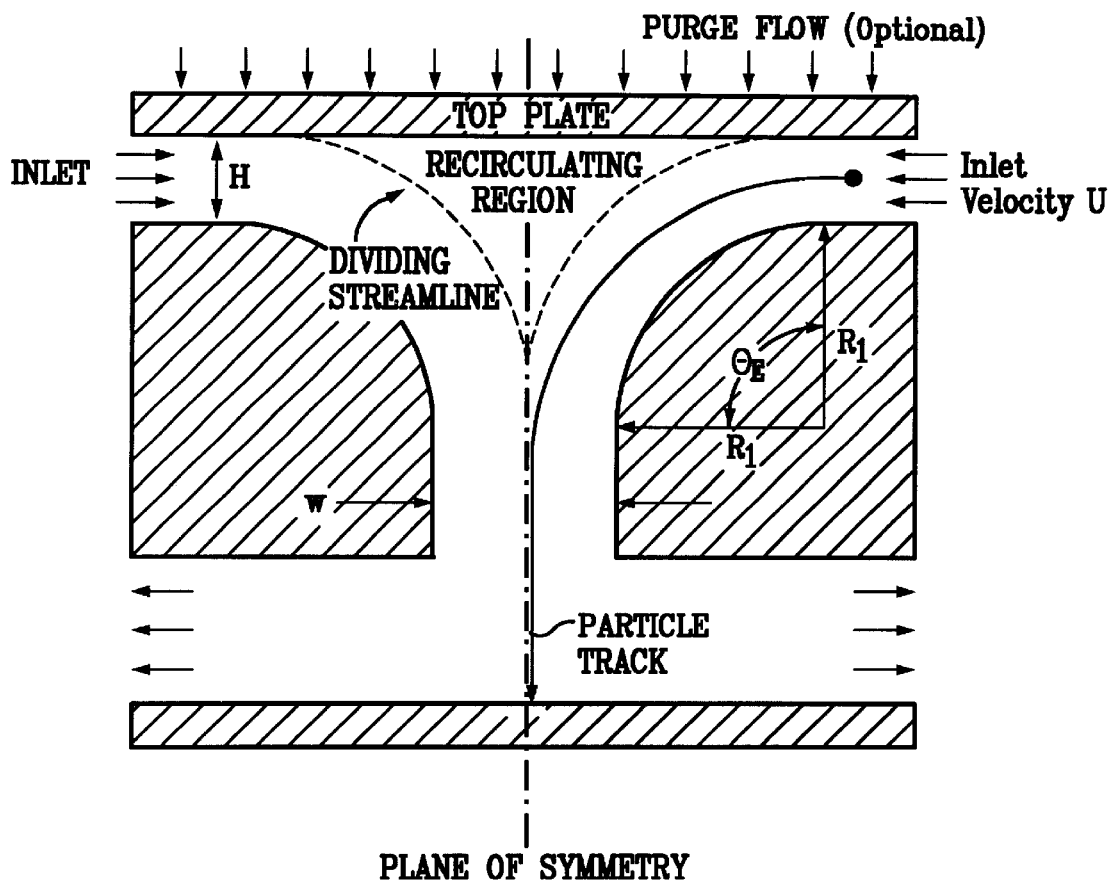
FIG. 3
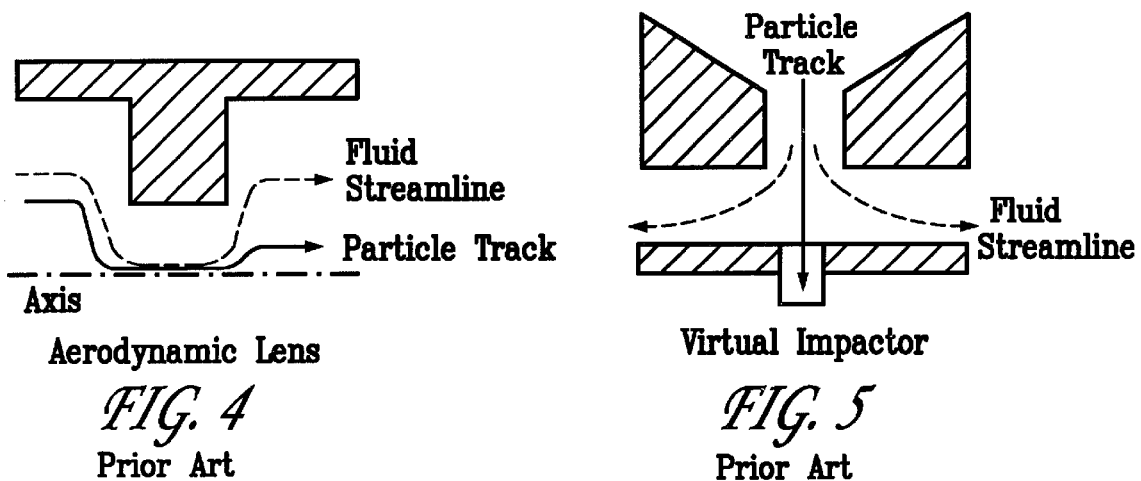
FIG. 4
Prior Art
FIG. 5
Prior Art

APPARATUS TO COLLECT, CLASSIFY, CONCENTRATE, AND CHARACTERIZE GAS-BORNE PARTICLES

CROSS REFERENCE TO RELATED APPLICATIONS

The present application is related to co-pending provisional application Ser. No. 60/151,815, filed Aug. 30, 1999, entitled "APPARATUS TO COLLECT, CLASSIFY, CONCENTRATE, AND CHARACTERIZE GAS-BORNE PARTICLES," from which priority is claimed under 35 USC §119(e).

STATEMENT OF GOVERNMENT INTEREST

The United States Government has rights in this invention pursuant to Contract No. DE-AC04-94AL85000 between the United States Department of Energy and the Sandia Corporation for the operation of the Sandia National Laboratories.

BACKGROUND OF THE INVENTION

Field of the Invention

The present invention is directed to collecting and characterizing gas-borne particles, particularly to the integration of an entire suite of discrete laboratory aerosol handling and characterization techniques into a single device. More particularly, this invention is directed to an "aerosol lab-on-a-chip" (ALOC) device, analogous to a microelectromechanical system (MEMS) device formed in silicon, by processes such as those described in U.S. Pat. Ser. Nos. 5,189,777, 5,331,236, and 5,455,547, and/or by advanced electrochemical and lithographic processes (Lithographic Galvanoforming Abforming or "LIGA") such as are described in U.S. Pat. Ser. Nos. 5,378,583, 5,631,514, and 5,917,260, all herein incorporated by reference.

These so-called MEMS or LIGA techniques are well known in the art, being similar to those used to produce the now familiar integrated circuit (IC), and have been shown to be capable of producing sub-millimeter to micron scale electrical/mechanical devices on a substrate of silicon. This technology has been exploited herein to integrate a variety of known aerosol processing techniques into a single package which is at once compact, rugged, self-contained, and inexpensive to manufacture. For convenience therefore, these LIGA and MEMS techniques will be collectively referred to throughout the remainder of the instant application as "micro-machining" techniques. In like manner, devices fabricated using these techniques shall likewise be referred to as "micro-machines."

A typical problem facing the aerosol field is that of collecting and characterizing gas-borne particles. As used here, the term "aerosol" refers to liquid or solid particles that are suspended in a gas (e.g., air). The particles may be anthropogenic (such as smog, fly ash, or smoke) or naturally occurring (such as pollens, dust, or mists). Sometimes the characterization of these gas-borne particles can be performed in situ (i.e., while the particles remain suspended in a gas), while in extractive techniques these particles are collected and then deposited onto a solid substrate or into a liquid for the purpose of subsequent physical or chemical analysis. Hereinafter, aerosol characterization is defined as the determination of the distribution of the size or shape, the chemical or biological composition, or any physical or chemical property of the suspended particles comprising the aerosol.

A large number of aerosol characterization techniques have been developed in the past. Examples of in situ instruments include those which infer particle size based on measurements of particle light scattering, (e.g. optical particle sizers or phase Doppler particle analyzers), on measurements of particle inertia (e.g. an aerodynamic particle sizer) or on measurements of particle electric mobility (e.g. differential mobility analyzers and electrical aerosol analyzers). Consequently, in situ techniques can provide detailed aerosol size distribution data (mass or number of suspended particles as a function of particle size per volume of gas). On the other hand, simple extractive instruments (e.g., jet impingers, jet impactors, cyclones, and filters) deposit particles onto a substrate with little or no size discrimination. For example, impactors and cyclones typically collect most particles larger than some characteristic diameter, while most smaller particles pass through. When detailed size distribution information is desired with these devices, the incoming aerosol first must be preconditioned in order to sort the particles according to size. In some cases, this sorting is accomplished by using a series of extractive devices that collect progressively smaller particles; examples include cascade inertial impactors or cascade cyclones.

The aerosol collection/analysis task is further complicated when only particles in a specific size interval are of interest. One such example is that of bioaerosols, which include air-borne pollens, viruses, or bacteria. Bioaerosols can result from natural processes (e.g., pollen releases by plants), or from human activities by inadvertent (e.g., in operating rooms, communicable diseases) or intentional (e.g., agricultural or battlefield) release. For example, bacteria typically range in size between about 1 and 5 microns, and it would be desirable to collect only particles in this size range to analyze airborne bacteria. Further complications to aerosol characterization arise when the concentration of particles of interest is very low (where particle concentration is given by the number of particles per unit volume of gas). Bioaerosols can again be used as an example; here the challenge is to separate bioaerosols from a potentially high concentration of background aerosol, ideally by removing the background particles and enriching the concentration of desired particles.

For aerosol characterization problems, the ideal aerosol instrument would be one which could accurately collect, classify, concentrate (enrich), and characterize particles in a variety of environments. The ideal instrument would also be compact, rugged, lightweight, and inexpensive, and would have low power consumption requirements. This instrument would provide a complete description of the aerosol size distribution, along with a determination of the particle chemical, physical, or biological composition distribution. Unfortunately, this ideal instrument does not currently exist. Currently, a complete description of an unknown aerosol relies on simultaneous or consecutive measurements using a combination of bench-top in situ or extractive instruments. Independent analytic techniques are often combined to help remove inherent ambiguities which result from the fact that most techniques do not directly measure true particle size, but in fact infer size from a direct measurement of some particle physical response. Each of these instruments must provide its own gas-handling, sensor, signal processing, and data acquisition capabilities (although many are now linked to computers); consequently, most of these systems are not compact, require line AC power, and are expensive. If more than one instrument is operated simultaneously, there always is the question as to whether all are analyzing the same aerosol due to potential upstream sampling and transport discrepancies.

The present invention provides one solution in the search for the ideal aerosol diagnostic tool, and involves an aerosol lab-on-a-chip (ALOC) in which a variety of aerosol collection, classification, concentration (enrichment), and characterization processes are all fabricated as needed onto a single substrate or layered stack of such substrates. By taking advantage of modern micro-machining capabilities, an entire suite of discrete laboratory aerosol handling and characterization techniques could be combined onto a single substrate, where they could be operated either serially or in parallel to perform a simultaneous characterization of the sampled aerosol. The ALOC is analogous to the integrated circuit, wherein a variety of discrete electronic (aerosol) components are combined onto a single chip to build-up complex electrical (aerosol characterization) systems. The performance of several of these analytic aerosol handling and characterization techniques would benefit by miniaturization (e.g., particularly the inertial techniques). By constructing arrays of identical parallel modules, it should be possible to reduce gas velocities that could give a quadratic reduction in pressure drop and consequently a quadratic reduction in power consumption. Sampling discrepancies would also be reduced; i.e., by virtue of their close proximity on the chip, each on-board characterization technique would be analyzing essentially the same aerosol sample.

SUMMARY OF THE INVENTION

It is an object of the invention to provide an aerosol diagnostic tool.

A further object of the invention is to provide a single device on which numerous aerosol characterization techniques may be carried out.

A further object of the invention is to provide a single apparatus that combines any of aerosol collection, classification, concentration (enrichment), and characterization processes.

Another object of the invention is to provide an aerosol lab-on-a-chip (ALOC) by advanced micro-machining capabilities wherein a suite of discrete laboratory aerosol handling and characterization techniques can be combined onto a single substrate or a layered stack of such substrates.

Another object of the invention is to provide an ALOC, where an entire suite of aerosol processing techniques can be operated either serially or in parallel to perform a simultaneous characterization of the sampled aerosol.

Another object of the invention is to provide an ALOC which is analogous to the integrated circuit wherein a variety of discrete aerosol (electronic) processing components are combined onto a single chip to build-up complex aerosol characterization (electrical) systems.

Another object of the invention is to provide an ALOC including arrays of identical parallel modules whereby gas velocities can be reduced which could give a quadratic reduction in pressure drop and consequently a quadratic reduction in power consumption.

Another object of the invention is to provide an ALOC whereby sampling discrepancies would be reduced, i.e., by virtue of their close proximity on the chip, each technique analyzes essentially the same aerosol sample.

Another object of the invention is to provide an ALOC that can be made sufficiently small and rugged to enable placement directly into harsh environments in which current laboratory equipment would not be operated.

Other objects and advantages of the present invention will become apparent from the following description and accompanying drawings. The present invention involves a single apparatus, formed on a substrate, or layered stack of such substrates, to collect, classify, concentrate, and characterize gas-borne particles. The invention described herein, provides a solution for an ideal aerosol diagnostic tool. The tool provides a variety of aerosol collection, classification, concentration (enrichment), and characterization processes are all fabricated, as needed, onto a single substrate or layered stack of such substrates, by well known advanced micro-machining techniques. The present invention, therefore, provides a method wherein an entire suite of discrete laboratory aerosol handling and characterization techniques can be combined onto a single substrate, or substrate stack, where they can be operated either serially or in parallel to perform a simultaneous characterization of the sampled aerosol. The ALOC reduces sampling discrepancies by virtue of their close proximity on the chip, each technique would be analyzing essentially the same aerosol sample. Gas-moving devices, such as pumps or fans, can be included to provide the gas throughput needed for the aerosol sampling and analysis in the absence of a moving gas stream. Use of such gas moving devices is necessary where insufficient gas flow exists in order to establish a flow of sufficient volume and velocity of gas through the characterization module(s) to ensure sampling an adequate number of particles to provide an accurate measurement. Electronic circuitry can also be fabricated onto the ALOC to provide for sensors, process control (valves, switches, etc.), signal processing, data analysis, and telemetry. The greatest advantage of the ALOC is the combination of a variety of aerosol processing and characterization techniques into a single, rugged, compact diagnostic that can provide a wealth of particle characterization data at relatively low cost.

BRIEF DESCRIPTION OF THE DRAWINGS

The accompanying drawings, which are incorporated into and form a part of the disclosure, illustrate an embodiment of the invention and, together with the description, serve to explain the principles of the invention.

FIG. 1 schematically illustrates an embodiment of the aerosol lab-on-a-chip (ALOC) of this invention on a single substrate.

FIG. 3 schematically illustrates an embodiment of an opposed-flow virtual cyclone.

FIG. 4 schematically illustrates an embodiment of an aerodynamic lens.

FIG. 5 schematically illustrates an embodiment of a virtual impactor.

DETAILED DESCRIPTION OF THE INVENTION

Figure 2B:
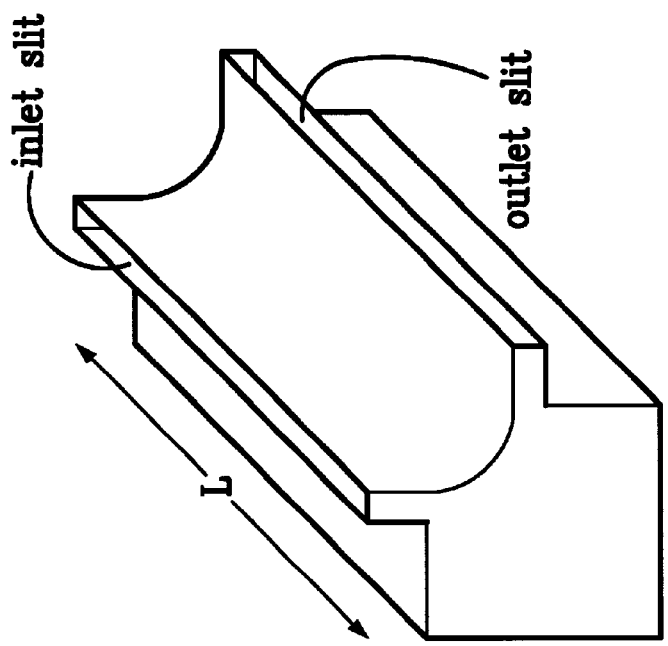
FIGS. 2A and 2B schematically illustrate a side view and a perspective view of an embodiment of a virtual cyclone.
Figure 2A:
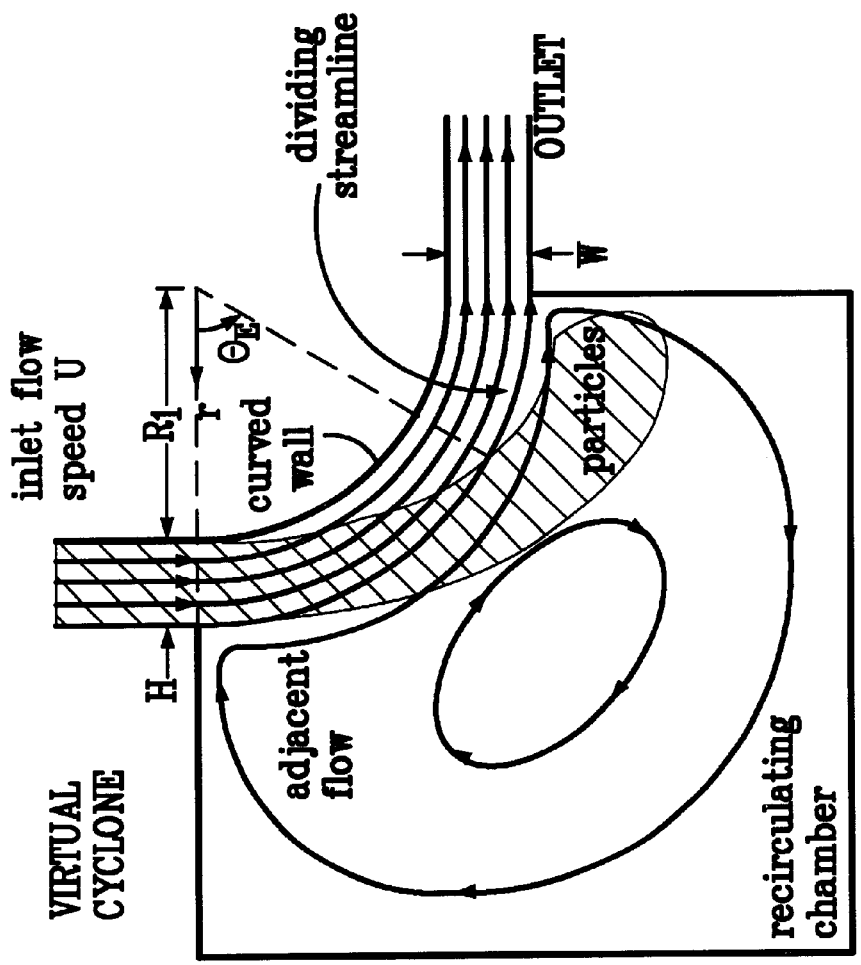

The present invention is directed to an aerosol diagnostic tool, particularly to an apparatus to collect, classify, concentrate, and/or characterize gas-borne particles. The aerosol diagnostic tool of this invention involves an aerosol lab-on-a-chip (ALOC). The basic principle underlying the ALOC is to take advantage of advanced micro-machining capabilities to integrate a variety of aerosol collection, classification, concentration (enrichment), and characterization processes into a single package which is compact, rugged, self-contained, and inexpensive to manufacture. Thus, a suite of discrete laboratory aerosol characterization techniques could be combined onto a single substrate, or stack of substrates, along with aerosol preconditioners and gas handling processes. The ALOC is analogous to the integrated circuit, wherein a variety of discrete electronic (aerosol) components are combined onto a single chip to build-up complex electrical (aerosol characterization) systems. The performance of several of these analytic aerosol characterization techniques would benefit by miniaturization (e.g., particularly the inertial techniques). By constructing arrays of identical parallel modules, it should be possible to reduce gas velocities that could give a quadratic reduction in pressure drop and consequently a quadratic reduction in power consumption. As pointed out above, sampling discrepancies would also be reduced; i.e., by virtue of their close proximity on the chip, each technique could be analyzing essentially the same sample. The performance of preconditioners, such as concentrators or size sorters, would also benefit by miniaturization, and could be built into layers above the diagnostics as needed. Gas-moving devices, such as pumps or fans, can be provided external to or fabricated onto the ALOC to provide the gas throughput needed for the aerosol sampling and analysis but are not essential. Electronic circuitry could also be fabricated onto the ALOC to provide for process control (valves, switches, etc.), signal processing, data analysis, and telemetry. Moreover, if the ALOC can be made sufficiently small and rugged, it could be placed directly into harsh (corrosive, high temperature, etc.) environments.

A schematic of an embodiment of the ALOC is shown for a single aerosol characterization technique in FIG. 1. The device components in the flow path are formed on a substrate 10, and comprise an aerosol inlet 11, an aerosol conditioner (preconditioner) 12, an aerosol characterization module 13, and a gas moving means, or "pump," 14, necessary in the absence of a moving gas stream, to establish a gas flow through the aerosol characterization module(s) of sufficient volume and velocity to ensure that an adequate number of particles are sampled. Pump 14 may be provided external to substrate 10, or it may be fabricated onto substrate 10 (onboard configuration is shown in FIG. 1). Preconditioner 12 may or may not be needed depending on the application. Support components are also shown which provide an active process control 15, signal processing/data analysis (signal processor) 16, and telemetry 17. The aerosol inlet 11 is designed to receive gas-borne particles from an ambient aerosol cloud 18. Note that none, some, or all of the support components 15, 16 and 17 may be needed for a particular characterization technique. Any number of characterization modules (and support processes) may be combined in parallel or in series on a single-chip or stacked-chip ALOC; by combining characterization modules based on independent physical measurements, it would be possible to perform simultaneous analysis of a wide array of particle properties. In addition, construction of parallel arrays of identical devices (i.e., multiple copies of FIG. 1) on a single substrate would have the advantage of providing, increased overall device efficiency, signal enhancement, and in particular, increased operational flexibility. For example, an ALOC could be made to handle high total gas flow rates by assembling large numbers of individual devices operating at low flow rates (with lower pressure drops).

Finally, power for the device is provided by a standard low-voltage source, such as a battery 19, through a set of leads 20 connected to a data/power bus 21 located on the integrated chip. Power also may be supplied by a battery incorporated directly onto the ALOC substrate, or by any other means known to those skilled in the art.

The functions of the individual components are described briefly now. 1) The aerosol inlet must provide a path that admits the particle-laden gas into the ALOC assembly. The shape of the inlet must be designed carefully, as is well known in the prior art, so as to avoid particle inertial inlet losses and to provide a suitable gas inlet velocity profile, and to avoid large pressure drops. 2) The term aerosol conditioner is used hereinafter to describe any collection of processes that may be used to either classify, concentrate, or in some way manipulate an incoming stream of particles comprising an aerosol prior to those particles reaching a characterization module. As a classifier, the conditioner can be used to accept or reject particles above or below a desired size, or within a desired size range. As a concentrator, the conditioner can be used to preferentially increase the local concentration of particles in a desired size range. 3) The purpose of the aerosol characterization module is to provide a measurement of some physical property of an individual particle or collection of particles. The characterization could be made based on any physical property of the particle, including prior art such as techniques based on particle light scattering, inertial response, or electric mobility. Many of the in situ or extractive techniques discussed above would be suitable for miniaturization. A complete characterization of the aerosol would require a determination of the distribution of size, shape, and chemical, physical, and biological composition of the suspended particles comprising the aerosol. 4) A gas moving device may be necessary, in the absence of a moving gas stream, in order to establish a flow of a sufficient volume and velocity of gas, and therefore, an adequate number of particles, through the characterization module(s) in order to ensure an accurate measurement. The gas moving device can be any means capable of generating a pressure differential such as a mechanical pump, a sorp pump, a fan, or ion or diffusion pumps, and can be external to or fabricated onto the ALOC. 5) Active process control would include sensors, circuitry, and control devices on-board the ALOC that would collectively act to maintain critical process parameters within acceptable operating ranges. Lumped into this module are additional flow handling devices, such as channels and valves, which may be needed to distribute/direct the gas flow among the various characterization modules. 6) Circuitry could also be provided to allow on-board signal processing or data analysis that would be used to reduce raw physical measurements from the aerosol characterization module into useful form. As an example, a pulse-height analyzer could be used to determine the peak scattering intensity needed to size a particle based on its scattering profile while passing through an illumination source. Systems could also be envisioned that would collect single-particle data and reduce it to obtain size distribution functions.

7) Telemetry could be used to send the acquired data to a remote collection unit. 8) Power to the ALOC is supplied by a standard low-voltage source, such as by a battery, which could be either external to, or built onto, the ALOC substrate.

The most obvious advantage to the ALOC is the combination of a variety of aerosol processing and characterization techniques into a single, rugged, compact, diagnostic that could provide a wealth of particle characterization data at relatively low cost. There are additional advantages, however, which accrue as the length scales of the various components are reduced. It should be noted that these advantages are gained with decreasing length scale generally independent of the fabrication technique (e.g., LIGA or MEMS). First, the reduction in length scale generally tends to suppress fluid turbulence and thereby allow for laminar flow, which results in lower particle deposition onto walls and makes prediction of particle trajectories deterministic. The determination of whether a flow is turbulent or laminar is typically guided by the magnitude of the non-dimensional Reynolds number, which is defined as:

$$Re = \frac{\rho U L}{\mu} \quad (1)$$

where $\rho$ and $\mu$ are the gas density and viscosity, respectively, and U and L are a characteristic velocity and length, respectively. As the characteristic length scale L becomes smaller, Re decreases which corresponds to increased laminarity of the flow. Note that further benefit is obtained by using micro-machine methods to construct arrays of large numbers of identical, parallel modules. In this case, the flow rate per module, and hence the characteristic velocity, can be reduced which again acts to reduce the Reynolds number and to stabilize the flow. Moreover, the reduction in gas velocities should lead to a nearly quadratic reduction in pressure drop and consequently to a quadratic reduction in power consumption.

Figure 6:
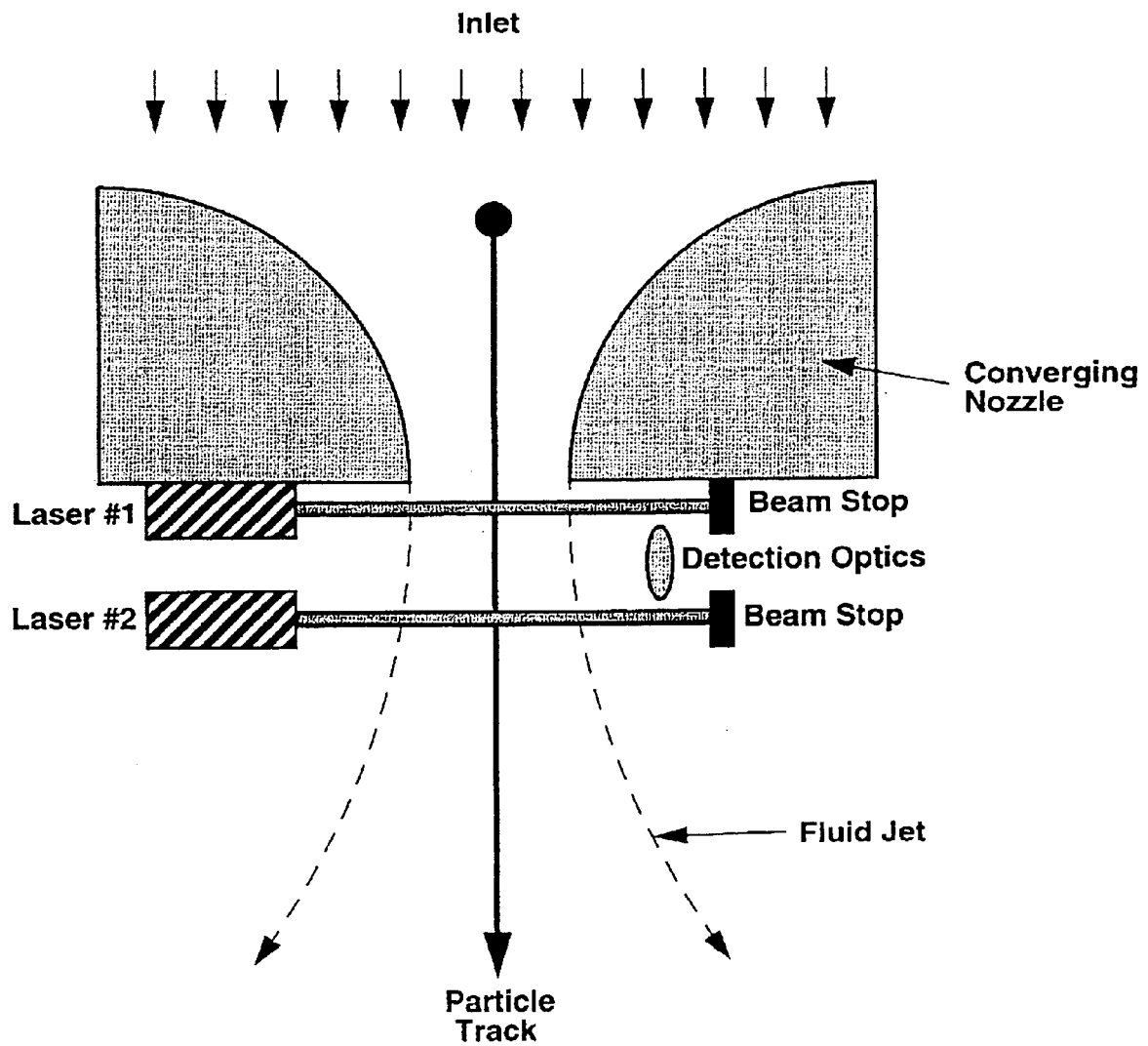
FIG. 6 illustrates a known technique for inferring the size of a particle by measuring its velocity lag in an accelerating gas stream.

Second, miniaturization could lead to improved performance of all inertial aerosol preconditioning and characterization processes. Specifically, miniaturization can be used in inertial systems to separate smaller particles at lower velocities (lower pressure drop and power consumption) compared to large-scale devices. This claim can be supported by considering the particle Stokes number, St, which is a non-dimensional number commonly used to characterize the performance of particle processes in which particle inertia is important:

$$St = \frac{C_{slip}\rho_p d_p^2 U}{18\mu L} \qquad (2)$$

where U and L are a characteristic system velocity and length, respectively, $C_{slip}$ is a factor that corrects for particle non-continuum drag ($C_{slip}$~1 for particles larger than about one micron at atmospheric conditions), $\rho_p$ and $d_p$ are the particle density and diameter, respectively, and is the gas viscosity. For most inertial devices there is a characteristic Stokes number (with magnitude of order unity) which generally divides particles which show an inertial response (those with larger Stokes numbers) from those which do not (those with smaller Stokes numbers). Equation (2) can be rearranged to show the corresponding characteristic diameter of a particle that will give an inertial response:

$$d_p = \sqrt{\frac{18\mu}{C_{slip}\rho_p}\frac{L}{U}St} \qquad (3)$$

It can be seen that inertial processes can be performed on ever smaller-sized particles by decreasing the characteristic system length, L. Also, for a fixed particle diameter of interest, the use of small-scale devices allows the separation to be achieved at lower velocities, which will reduce pressure drop and consequently pumping power requirements. The principle of using small-sized devices to inertially separate very small particles is well known in the art, such as in the commercially available MicroOrifice Uniform Deposit Impactor (Marple, Rubow, and Behm, 1991, "A Microorifice Uniform Deposit Impactor (MOUDI); Description, Calibration, and Use," *Aerosol Sci. Technol.* 14(4): 434–446). Clearly, the opportunity to work at small length scales which is afforded by the advent of micro-machined devices offers many new opportunities for inertially-based particle preconditioning and characterization techniques. As an example, recent analyses of particle focusing with either a standard or an Opposed-Flow Virtual Cyclone showed that miniaturization would allow concentration of smaller particles at lower pressure drops.

The improved performance resulting from miniaturization is discussed below for several specific aerosol preconditioners and characterization techniques. These examples are intended to support the claim that miniaturization can be used to improve process performance; additional processes could also be miniaturized With benefits that would be apparent for one skilled in the art.

Virtual cyclone:

One candidate for a micro-preconditioner is the virtual cyclone, which was recently presented (Torczynski and Rader, 1997, "The Virtual Cyclone: A Device for Nonimpact Particle Separation," *Aerosol Sci. Technol.*, 26: 560–573) as a means of separating particles from a main flow and concentrating them in an adjacent recirculating chamber. In the virtual cyclone, the main particle-laden flow follows a wall that curves away from the original flow direction, as shown in FIG. 2. Although a wall forms the inner boundary of the main flow, its outer boundary is formed by an adjacent flow, often a confined recirculating flow, into which particles are transferred by centrifugal action. Thus, in the virtual cyclone, particles are separated from the main flow by crossing a dividing streamline that separates the main flow stream from an adjacent flow stream. If a confined recirculating chamber geometry is used, particle concentrations in the recirculating region can be greatly increased relative to the main stream. Two primary advantages of the virtual cyclone are that it: 1) accomplishes inertial separation in such a way as to greatly reduce particle deposition on the walls, and 2) the separated, concentrated particles remain suspended in the gas in the recirculating chamber, from which they may be extracted for subsequent conditioning or characterization. Recent experiments have shown that the virtual cyclone performs well at low Reynolds numbers, but that turbulent mixing produced by shear-layer roll-up can limit particle-concentration enhancements at high flow Reynolds numbers (Torczynski, O'Hern, Rader, Brockmann, and Grasser, 1998, "An Experimental Investigation of the Flow in a Virtual Cyclone," Sandia National Laboratories Report #SAND98-2004). In the "Discussion" section of that report, the authors note that the construction of a small-scale virtual cyclone would be one way to obtain the desired laminar flow (based on arguments of using small physical length scales to keep the Reynolds number low, as discussed above). In addition, the authors reported that the use of small-scales would also allow the virtual cyclone to separate smaller particles and with lower power consumption than a large-scale virtual cyclone (based on arguments related to the Stokes number, as discussed above).

Opposed-Flow Virtual Cyclone:

A second candidate for a micro-preconditioner is the opposed-flow virtual cyclone (OFVC), recently disclosed and claimed as a means to accurately concentrate (enrich) particles in a size range of interest (D. Rader and J. Torczynski, co-pending U.S. application Ser. No. 09/244,259 filed Feb. 3, 1999, herein incorporated by reference). A schematic of one embodiment of the opposed-flow virtual cyclone (OFVC) is shown in FIG. 3. In simplest terms, the device consists of two geometrically similar virtual cyclones arranged such that their inlet jets (of width H) are inwardly directed and symmetrically opposed relative to a plane of symmetry located midway between the two inlet slits. As shown in FIG. 3 a top plate bounds both jets on the "top" side of the inlets, while the other wall of the inlet curves "down" and away from each inlet jet (note that the descriptions of the OFVC are relative to the orientation shown in FIG. 3, although the OFVC could in principle be operated in any orientation). As in the standard virtual cyclone, the underlying principle of the OFVC is that each inlet jet will follow the adjacent lower wall as it turns away, and that particles will be transferred away from the wall and towards the plane of symmetry by centrifugal action. After turning, the two jets merge smoothly along the plane of symmetry and flow parallel to it ("downward") through the throat of width W. For a solid top plate, a recirculation region will form between the two jets (i.e., about the symmetry plane, below the top plate, and above the point at which the two jets merge). Thus, in this embodiment of the OFVC, particles are transferred from the main flows, across the dividing streamlines, and into the central recirculating region, where particle concentrations become greatly increased relative to the main stream. Eventually particles will leak out of the recirculation zone, and these particles will be highly focused into a narrow region about the symmetry plane between the two converging flows. Additional embodiments include: 1) the use of a small flow through a porous top plate for the purpose of purging particles from the recirculating region, and 2) to vary the shape of the lower wall used to turn the flow (in FIG. 3 the lower wall is depicted as a quarter circle). Strictly speaking, the OFVC ends at the end of the throat, where the exiting particles are concentrated into a narrow region about the flow plane of symmetry. Thus, the OFVC operates as a pre-conditioner, and a variety of options could be envisioned downstream. For example, the exiting jet could impinge on a solid, normal plate such as in a traditional impactor, or onto a small pool of liquid in the plate along the symmetry plane, such as in an impinger. A characterization module could also accept the focused aerosol, as the problem of "finding" the particle has been significantly reduced. Additional variations could be imagined by one skilled in the art.

One advantage of the OFVC is that it will concentrate particles only within a particular size range. If particles are too small, they will tend to follow the main flow instead of being centrifuged across the dividing streamline. If particles are too large, they will overshoot the recirculating region and pass into the opposing jet, and thereby resist focusing. Strategies for designing an OFVC that will only concentrate particles within a particular size range are described in the above referenced co-pending U.S. patent application Ser. No. 09/244,259. Based on that analysis, it is clear that micro-machining methods could be used to make small gaps, H, which allow collection of smaller particles at reduced pressure drops. For example, the potential of using small sized micro-machined gaps to allow low-pressure operation, or to allow separation of very small sized particles was considered. The advantages of using a small inlet jet are based on the same Stokes number argument given above. The above referenced co-pending application showed that the Stokes number for the minimum-sized particle that can be effectively separated from the main flow in a virtual cyclone geometry (either standard or opposed-flow) could be approximated by St~$1/\theta_E$ where $\theta_E$ is the total angle that the main flows turn through ($\theta_E=\mu/2$ for the OFVC shown in FIG. 3). Consequently, Equation (3) gives the minimum size particle that can be completely separated from the main flow in a virtual cyclone:

$$d_{p,\min} = \sqrt{\frac{18\mu}{C_{slip}\rho_p}\cdot\frac{H}{U\theta_E}} = \sqrt{\frac{36\mu}{\pi C_{slip}\rho_p}\cdot\frac{H}{U}} \tag{4}$$

where the final equality is for the case $\theta_E=\mu/2$ shown in FIG. 3. From Equation (4), it is clear that smaller particles can be separated from the main flow (i.e., concentrated about the centerline) by decreasing the inlet slit width, such as by using micro-machined devices. In particular, one series of design specifications was presented in Table 1 of the above-referenced co-pending application Ser. No. 09/244,259 which showed that particles down to 1.5 micron could be separated at very low pressure differentials (less than 0.25 inches of water) if the inlet gap was kept smaller than about 0.1 mm.

Other Inertia-Based Preconditioning:

Based on the previous Stokes-number arguments, the use of small physical feature size should allow any inertia-based particle process to be applied at smaller particle sizes and lower pressure drops. For example, one approach to aerosol enrichment is the aerodynamic lens, which concentrates particles along the centerline of an axisymmetric geometry through a series of flow contractions and enlargements (Peng, et al., 1995, *Aerosol Sci. Technol.*, 22:293–313 and 314–324); a schematic is shown in FIG. 4. After each contraction, particles are moved closer to the centerline if their aerodynamic sizes are less than a critical size, while particles larger than the critical size move farther from the centerline. Through a careful design of a series of lenses, particle enrichment within a specific size range can be achieved. Although the aerodynamic lens has already been demonstrated, the advantages of miniaturizing it or including it as a discrete component in an ALOC device have not been explored. Another means of achieving particle enrichment is the virtual impactor, which generally consists of an axisymmetric jet impinging on a normal plate which has a small hole (perhaps leading to a cavity below) in it located at the jet centerline (Marple and Chien, 1980, *Environ. Sci. Technol.*, 14: 976–985); for a schematic see FIG. 5. If flow through the hole is restricted, then the region behind the hole becomes a stagnation zone, which acts as a "virtual surface." Thus, the impinging jet is deflected by the plate (and the virtual surface at its center) and flows out radially. Because of their inertia, particles cannot make the turn and are impacted into the virtual surface, leading to particle enrichment in the cavity below. By careful design of a series of virtual impactor stages, particle enrichment in a specific size range can be achieved. Again, a miniaturized virtual impactor could separate smaller sized particles at lower pressure drops. Other inertia-based devices that would benefit from miniaturization include impactors, cyclones, and impingers. This benefit of small-scale feature size has at least been recognized in the impactor community, as evidenced by the MOUDI impactor discussed above. The combination and integration of a variety of such preconditioners onto a single ALOC device has not yet been recognized.

Microscale Aerosol Characterization Techniques:

After a review of the problem, it became apparent that many of the current laboratory-scale aerosol characterization techniques could be miniaturized, and furthermore, that many of these techniques might actually perform better at reduced scale. Based on the above Stokes-number discussion, characterization methods based on measurement of particle inertial properties would appear to be excellent candidates for miniaturization. One commercial instrument, the aerodynamic particle sizer (APS, offered by TSI, St. Paul, Minn.) infers particle size based on the velocity lag between a particle and an accelerating gas such as in the flow of a converging nozzle; a schematic is shown in FIG. 6. Based on Stokes-number arguments, this technique should be able to characterize smaller particles with lower pressure drops as the nozzle diameter is decreased. Particle velocity is measured based on the particle time-of-flight between two laser sheets oriented normal to the direction of flow and positioned at the nozzle exit; recent advances in small-scale lasers and optics could conceivably allow this entire device to be fabricated on a single substrate. Optical particle counters (OPC) infer particle size based on the peak intensity of light scattered as a particle passes through a region illuminated by high-intensity (usually laser) light. Recent advances in miniaturized laser sources and detectors should allow fabrication of an OPC-on-a-chip, although no particular advantage in performance would likely result. Note that the performance of both APS and OPC techniques could be significantly improved if preceded by an aerosol conditioner, such as OFVC.

A complete consideration of the pros and cons of miniaturization of standard laboratory-scale aerosol characterization techniques has not been undertaken. The above examples are offered only to show the feasibility of fabricating single-chip aerosol characterization devices.

Instead of performing an aerosol characterization with a set of discrete, laboratory-scale instruments, the ALOC proposes integrating a variety of aerosol collection, classification, concentration (enrichment), and characterization processes onto a single substrate or layered stack of such substrates. By taking advantage of modern micro-machining capabilities, an entire suite of discrete laboratory aerosol handling and characterization techniques could be combined in a single, portable device that would provide a wealth of data on the aerosol being sampled.

The ALOC, therefore, offers the following advantages over existing technology, in that:

1.) it integrates an entire suite of discrete laboratory aerosol handling and characterization techniques into a single device;

2.) its benefits are analogous to those of an integrated circuit, wherein a variety of discrete electronic (aerosol) components are combined onto a single chip to allow increased flexibility;

3.) when using parallel characterization techniques, the close proximity of the various characterization modules helps ensure that the same aerosol is available to all devices dramatically reducing sampling errors and transport losses;

4.) micro-machine fabrication of the ALOC significantly reduces unit costs relative to existing technology;

5.) micro-machine fabrication produces or makes a small, portable ALOC device;

6.) the ALOC offers potential for rugged design to allow operation in harsh environment;

7.) on-board signal processing, data analysis, and telemetry would allow remote operation of an ALOC device; and 8.) when using inertia-based preconditioning and characterization techniques, miniaturization offers the potential of working with smaller particle sizes and lower pressure drops (leading to reductions in power consumption).

While a particular embodiment of the invention has been illustrated and described and modifications have been described, such are not intended to be limiting. Modifications and changes may become apparent to those skilled in the art, and it is intended that the invention be limited only by the scope of the appended claims.

What is claimed is:

1. An apparatus for manipulating particles comprising an aerosol, said apparatus comprising:

a substrate;

an aerosol inlet for receiving said particles, wherein said aerosol inlet is made on said substrate; and an aerosol characterization module for providing a signal response corresponding to a property of said particles, wherein said aerosol characterization module is made on said substrate and in fluid communication with said aerosol inlet.

2. The apparatus, of claim 1, further comprising a gas moving means for assisting in drawing a portion of said particles through said apparatus, said gas moving means in fluid communication with said aerosol inlet and said aerosol characterization module.

3. The apparatus, of claim 2, wherein said gas moving means is a mechanical pump, a sorp pump, a fan, or any means for establishing a flow of particles through said apparatus.

4. The apparatus of claim 3, wherein said gas moving means is made on said substrate.

5. The apparatus of claim 1, wherein said apparatus is made by using a micro-machining process.

6. The apparatus of claim 1, further comprising an aerosol preconditioner, said aerosol preconditioner for providing means for classifying, sorting, grouping, concentrating, or focusing a portion of said particles, said aerosol preconditioner located on said substrate, between, and in fluid communication with, of said aerosol inlet and said aerosol characterization module.

7. The apparatus of claim 6, wherein said apparatus is made by using a micro-machining process.

8. The apparatus of claim 6, wherein said substrate comprises a plurality of substrates.

9. The apparatus of claim 8, wherein said plurality of substrates is a layered stack of substrates.

10. The apparatus of claim 9, wherein said apparatus is made by using a micro-machining process.

11. The apparatus of claim 1, further including one or more support components selected from the group consisting of an active process controller, a signal processor/data analyzer, and a telemetry unit, and combinations thereof, wherein said support components are in electrical communication with each other and with said aerosol characterization module, and wherein further said support components are made on said substrate.

12. The apparatus of claim 11, further including a gas moving means selected from the group consisting of a mechanical pump, a sorp pump, a fan, and equivalent means for establishing a flow of particles through said apparatus, said gas moving means in fluid communication with said aerosol inlet and said aerosol characterization module.

13. The apparatus of claim 11, wherein said apparatus is made by using a micro-machining process.

14. The apparatus of claim 11, wherein said substrate comprises a plurality of substrates.

15. The apparatus of claim 14, wherein said plurality of substrates is a layered stack of substrates.

16. The apparatus of claim 15, wherein said apparatus is made by using a micro-machining process.

17. The apparatus of claim 12, wherein said process controller comprises integrated microcircuitry devices selected from the group consisting of sensors, control devices, flow handling devices, and combinations thereof, said sensors, control devices, and flow handling devices collectively acting to control flow through and operation of said apparatus, said sensors, control devices, and flow handling devices in electrical communication with said characterization module and said gas moving means.

18. The apparatus of claim 11, wherein said signal processor includes integrated microcircuitry to receive a digital or analog signal generated by said aerosol characterization module, to arithmetically manipulate and interpret said digital or analog signal so as to provide a predefined output response and to provide said output response to said telemetry unit.

19. The apparatus of claim 11, further including a source of electrical power.

20. The apparatus of claim 12, further including a source of electrical power.

21. The apparatus of claim 6, further including one or more support components selected from the group consisting of an active process controller, a signal processor/data analyzer, and a telemetry unit, and combinations thereof, wherein said support components are in electrical communication with each other and with said aerosol preconditioner and said aerosol characterization module, and wherein further said support components are made on said substrate.

22. The apparatus of claim 21, further including a gas moving means selected from the group consisting of a mechanical pump, a sorp pump, a fan, and equivalent means for establishing a flow of particles through said apparatus, said gas moving means in fluid communication with said aerosol inlet, said aerosol preconditioner, and said aerosol characterization module.

23. The apparatus of claim 21, wherein said apparatus is made by using a micro-machining process.

24. The apparatus of claim 21, wherein said substrate comprises a plurality of substrates.

25. The apparatus of claim 24, wherein said plurality of substrates is a layered stack of substrates.

26. The apparatus of claim 25, wherein said apparatus is made by using a micro-machining process.

27. The apparatus of claim 22, wherein said active process controller comprises integrated microcircuitry devices selected from the group consisting of sensors, control devices, flow handling devices, and combinations thereof, said sensors, control devices, and flow handling devices collectively acting to control flow through and operation of said apparatus, said sensors, control devices, and flow handling devices in electrical communication with said preconditioner, said characterization module, and said gas moving means.

28. The apparatus of claim 21, wherein the signal processor includes integrated microcircuitry to receive a digital or analog signal generated by said aerosol characterization module, to arithmetically manipulate and interpret said digital or analog signal so as to provide a predefined output response and to provide said output response to said telemetry unit.

29. The apparatus of claim 21, further including a source of electrical power.

30. The apparatus of claim 22, further including a source of electrical power.

31. The apparatus of claim 1, additionally including at least a second aerosol characterization module on said substrate, wherein said aerosol characterization modules are combined either in parallel or in series to enable simultaneous analysis of a plurality of properties of said particles.

32. The apparatus of claim 31, wherein said substrate is a layered stack of substrates.

33. The apparatus of claim 32, wherein said apparatus is made by using a micro-machining process.

34. The apparatus of claim 6, further comprising a plurality of aerosol preconditioners and a plurality of associated aerosol characterization modules wherein said aerosol preconditioners and said associated aerosol characterization modules are arranged in an array made on said substrate.

35. The apparatus of claim 34, wherein said substrate is a layered stack of substrates.

36. The apparatus of claim 35, wherein said apparatus is made by using a micro-machining process.

37. An aerosol lab-on-a-chip (ALOC) device made by the method comprising the steps of:
providing a substrate;
forming an aerosol inlet on said substrate, said aerosol inlet for receiving particles comprising an aerosol; and
forming at least one aerosol characterization module on said substrate, wherein said aerosol inlet and said at least one aerosol characterization module are in fluid communication, said aerosol characterization module for providing a signal response corresponding to a property of said particles.

38. The device made by the method of claim 37, further including the step of providing a gas moving means for assisting in drawing at least some of said particles through said device, wherein said gas moving means is selected from the group consisting of a mechanical pump, a sorp pump, a fan, or equivalent means, and wherein said aerosol inlet, said at least one aerosol characterization module and said gas moving means are in fluid communication.

39. The device made by the method of claim 37, wherein said steps of forming are carried out using a micromachining process.

40. The device made by the method of claim 38, further including the step of forming at least one aerosol preconditioner on said substrate, wherein said preconditioner is located between, and in fluid communication with, said aerosol inlet and said at least one aerosol characterization module.

41. The device made by the method of claim 40, wherein said step of forming is carried out using a micromachining process.

42. The device made by the method of claim 40, wherein said step of forming at least one aerosol preconditioner on said substrate further includes forming said aerosol inlet, said at least one aerosol preconditioner, and said at least one aerosol characterization module on a layered stack of substrates.

43. The device made by the method of claim 42, wherein said steps of forming are carried out using a micromachining process.

44. The device made by the method of claim 40, wherein said step of forming at least one aerosol preconditioner on said substrate further includes the step of forming one or more support components selected from the group consisting of a process controller, a signal processor, and a telemetry unit, and combinations thereof, said support components in electrical communication with each other and with said at least one aerosol preconditioner and said at least one aerosol characterization module.

45. The device made by the method of claim 44, wherein said step of forming said process controller comprises forming one or more integrated microcircuitry devices selected from the group consisting of sensors, control devices, flow handling devices, and combinations thereof, said sensors, control devices, and flow handling devices collectively acting to control said gas flow through, and operation of, said ALOC device, said sensors, control devices, and flow handling devices in electrical communication with said at least one aerosol characterization module and said at least one aerosol preconditioner.

46. The device made by the method of claim 44, wherein said step of forming said signal processor includes forming one or more integrated microcircuitry devices to receive a digital or analog signal generated by said characterization module, to arithmetically manipulate and interpret said signal so as to provide a predefined output response, and to output said response to said telemetry.

47. The device made by the method of claim 44, further including the step of providing a source of electrical power.

48. The device made by the method of claim 44, wherein said steps of forming are carried out using a micromachining process.

49. The device made by the method of claim 42, wherein said step of forming at least one aerosol preconditioner on said substrate further includes the step of forming one or more support components selected from the group consisting of a process controller, a signal processor, and a telemetry unit, and combinations thereof, said support components in electrical communication with each other and with said at least one aerosol preconditioner and said at least one aerosol characterization module.

50. The device made by the method of claim 49, further including the step of providing a gas moving means, wherein said gas moving means is selected from the group consisting of a mechanical pump, a sorp pump, a fan, and equivalent means for establishing a flow of particles through said device, and wherein said gas moving means is in fluid communication with said aerosol inlet, said at least one aerosol preconditioner, and said at least one aerosol characterization module.

51. The device made by the method of claim 49, wherein said step of forming said process controller comprises forming one or more integrated microcircuitry devices selected from the group consisting of sensors, control devices, flow handling devices, and combinations thereof, said sensors, control devices, and flow handling devices collectively acting to control flow into said at least one aerosol characterization module, said sensors, control devices, and flow handling devices in electrical communication with said at least one aerosol preconditioner and said at least one aerosol characterization module.

52. The device made by the method of claim 49, wherein said step of forming said signal processor includes forming one or more integrated microcircuitry devices to receive a digital or analog signal generated by said characterization modules, to arithmetically manipulate and interpret said signal so as to provide a predefined output response, and to output said response to said telemetry.

53. The device made by the method of claim 49, further including the step of providing a source of electrical power.

54. The device made by the method of claim 49, wherein said step of forming is carried out using a micromachining process.

55. The device made by the method of claim 37, additionally including the step of forming at least a second aerosol characterization module on said substrate, wherein said aerosol characterization modules are combined in either in parallel or in series to enable simultaneous analysis of a plurality of properties of said particles.

56. The device made by the method of claim 40, further comprising the step of forming a plurality of aerosol preconditioners and a plurality of associated aerosol characterization modules on said substrate wherein said plurality of aerosol preconditioners and said plurality of associated aerosol characterization modules are arranged in an array.

57. The device made by the method of claim 42, further comprising the step of forming a plurality of aerosol preconditioners and a plurality of associated aerosol characterization modules on said layered stack of substrates, wherein said plurality of aerosol preconditioners and said plurality of associated aerosol characterization modules are arranged in an array.

58. An aerosol lab-on-a-chip (ALOC) machine comprising:

a plurality of devices comprising:

an aerosol inlet for receiving particles comprising an aerosol; and an aerosol characterization module for providing a signal response corresponding to a property of an individual particle or collection of particles, said aerosol characterization module in fluid communication with said aerosol inlet;

wherein, said devices are arranged in an array fashion and wherein each said device is linked to one or more other devices either in parallel or in series.

59. The machine of claim 58, wherein said devices are fabricated by a micro-machining process and formed onto a single substrate or a layered stack of substrates.

60. The machine of claim 58, further comprising a gas moving means seleted from the group consisting of a mechanical pump, a sorp pump, a fan, and equivalent means for establishing a flow of particles through said machine.

61. The machine of claim 58, additionally including:

a process controller formed on said substrate and operatively connected to said array of devices;

a signal processor formed on said substrate and in communication with said plurality of aerosol characterization modules; and a telemetry unit formed on said substrate and operatively connected to said signal processor.

* * * * *